(12) United States Patent
Torjesen et al.

(10) Patent No.: US 12,376,911 B2
(45) Date of Patent: Aug. 5, 2025

(54) INTERVENTIONAL MEDICAL DEVICE TRACKING

(71) Applicant: KONINKLIJKE PHILIPS N.V., Eindhoven (NL)

(72) Inventors: Alyssa Torjesen, Exeter, NH (US); Molly Lara Flexman, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 62 days.

(21) Appl. No.: 18/026,949

(22) PCT Filed: Sep. 18, 2021

(86) PCT No.: PCT/EP2021/075736
§ 371 (c)(1),
(2) Date: Mar. 17, 2023

(87) PCT Pub. No.: WO2022/069266
PCT Pub. Date: Apr. 7, 2022

(65) Prior Publication Data
US 2023/0255695 A1    Aug. 17, 2023

Related U.S. Application Data

(60) Provisional application No. 63/085,357, filed on Sep. 30, 2020.

(51) Int. Cl.
*A61B 34/20* (2016.01)
*A61B 90/00* (2016.01)

(52) U.S. Cl.
CPC ...... *A61B 34/20* (2016.02); *A61B 2034/2061* (2016.02); *A61B 2090/364* (2016.02); *A61B 2090/376* (2016.02); *A61B 2090/378* (2016.02)

(58) Field of Classification Search
CPC ............ A61B 34/20; A61B 2034/2061; A61B 2090/364; A61B 2090/376; A61B 2090/378; A61B 2034/102
See application file for complete search history.

(56) References Cited

U.S. PATENT DOCUMENTS

| 9,687,204 B2 | 6/2017 | Mountney |
| 9,710,921 B2 | 7/2017 | Wong |
| 2022/0218302 A1 | 7/2022 | Torjesen |

FOREIGN PATENT DOCUMENTS

| CN | 107854177 A | 3/2018 |
| EP | 2663237 A1 | 11/2013 |

(Continued)

OTHER PUBLICATIONS

International Search Report and Written Opinion Dated Jan. 5, 2022 For International Application No. PCT/EP2021/075736 Filed Sep. 18, 2021.

*Primary Examiner* — Alexei Bykhovski

(57) ABSTRACT

A system includes an interface (193) to an optical shape sensing device (102) with a shape conforming to a shape of an interventional medical device (01). The system also includes a controller (190) with a memory (191) that stores instructions and a processor (192) that executes the instructions. The instructions cause the system to identify a shape of the optical shape sensing device (102) using optical shape sensing signals received via the interface (193), identify the interventional medical device (01) in disparate coordinate spaces of imaging systems that image the interventional medical device (01) in disparate imaging modes, and register the coordinate spaces to each other and to the interventional medical device (01). The instructions also cause the system to obtain a segmented representation (401) of the interventional medical device (01), and re-register the interventional medical device (01) to one of the coordinate space (Continued)

based on registering the interventional medical device (01) to another of the coordinate spaces using the segmented representation (401).

15 Claims, 9 Drawing Sheets

(56) References Cited

FOREIGN PATENT DOCUMENTS

| | | |
|---|---|---|
| EP | 2903552 A1 | 8/2015 |
| EP | 3434192 A1 | 1/2019 |
| EP | 3542747 A1 | 9/2019 |
| WO | 2012095784 A1 | 7/2012 |
| WO | 2014053925 A1 | 4/2014 |
| WO | 2016/088037 A1 | 6/2016 |
| WO | 2020/182997 A1 | 9/2020 |

INTERVENTIONAL MEDICAL DEVICE TRACKING

CROSS REFERENCE TO RELATED APPLICATIONS

This application is the U.S. National Phase application under 35 U.S.C. § 371 of International Application No. PCT/EP2021/075736 filed Sep. 18, 2021, which claims the benefit of U.S. Provisional Patent Application No. 63/085,357 filed Sep. 30, 2020. These applications are hereby incorporated by reference herein.

BACKGROUND

Optical shape sensing technology (OSS) is used to provide real-time, intra-procedural information of the shape and relative location of an interventional medical device in an interventional medical procedure. The information from OSS is used to localize and navigate the interventional medical device during the interventional medical procedure. OSS uses light along a multicore optical fiber that conforms to the shape of the interventional medical device during the interventional medical procedure. The principle involved makes use of distributed strain measurements in the optical fiber using characteristic Rayleigh backscatter or controlled grating patterns. The shape along the optical fiber begins at a specific point, known as the launch, or z=0, and the subsequent shape, position and orientation are relative to the launch. Separately, registration is used to align the coordinate systems of two separate devices and/or systems. For example, registration from an OSS device to an X-Ray imaging system can be accomplished via a transform $T_{OX}$ from the OSS device to the X-Ray imaging system. Registration from an ultrasound imaging system to the X-Ray imaging system can be accomplished via a transform $T_{UX}$ from the ultrasound imaging system to the X-Ray imaging system. Registration from the OSS device to the ultrasound imaging system can be accomplished via a transform $T_{OU}$ from the OSS device to the ultrasound imaging system.

Additionally, segmentation is used in medical imaging systems to represent surfaces of structures as three-dimensional models.

Currently, registration between the OSS device and the X-Ray imaging system may accumulate a noticeable error, such as when the proximal end of the OSS device (i.e., nearest the user) is moved several centimeters. Correction of the error requires re-registration between the OSS device and the X-Ray imaging system, which in turn requires two new offset X-Ray projections. The additional X-Ray projections may interrupt the flow of the interventional medical procedure, may extend the time of the interventional medical procedure, and subject the patient and clinician to additional X-Ray dosages.

Registration between the OSS device and the ultrasound imaging system may also accumulate a notice error. Re-registration between the OSS device and the ultrasound imaging system may interrupt the flow of the interventional medical procedure and extend the time of the interventional medical procedure while image analysis software searches through the latest ultrasound imagery for the OSS device. The image analysis software may require a designation of the OSS device in the ultrasound imagery, such as from a designation of a tip of the OSS device in the ultrasound imagery by a user, in order to constrain a search for the OSS device in the ultrasound imagery. Even with an initial constraint, the OSS device must be fully identified and located in the ultrasound imagery for the re-registration between the OSS device and the ultrasound imaging system, and this interrupts the flow of the interventional medical procedure and extends the time of the interventional medical procedure.

SUMMARY

According to an aspect of the present disclosure, a system for tracking location of an interventional medical device in an interventional medical procedure includes an interface and a controller. The interface interfaces an optical shape sensing device which has a shape that conforms to a shape of the interventional medical device during the interventional medical procedure. The controller includes a memory that stores instructions and a processor that executes the instructions. When executed by the processor, the instructions cause the system to identify a shape of the optical shape sensing device using optical shape sensing signals received from the optical shape sensing device via the interface, and identify the interventional medical device in a first coordinate space of a first imaging system that images the interventional medical device in a first imaging mode during the interventional medical procedure, based on identifying the shape of the optical shape sensing device. The instructions also cause the system to register the interventional medical device to the first coordinate space, identify the interventional medical device in a second coordinate space of a second imaging system that images the interventional medical device in a second imaging mode during the interventional medical procedure, and register the first coordinate space of the first imaging system to the second coordinate space of the second imaging system. The instructions further cause the system to segment the interventional medical device in the second coordinate space to obtain a segmented representation of the interventional medical device in the second coordinate space, register the interventional medical device to the second coordinate space using the segmented representation of the interventional medical device, and re-register the interventional medical device to the first coordinate space based on registering the interventional medical device to the second coordinate space.

According to another aspect of the present disclosure, a tangible non-transitory computer readable storage medium stores a computer program. The computer program, when executed by a processor, causes a system that includes the tangible non-transitory computer readable storage medium to identify a shape of the optical shape sensing device using optical shape sensing signals received via an interface from an optical shape sensing device which has a shape that conforms to a shape of the interventional medical device during the interventional medical procedure, and to identify the interventional medical device in a first coordinate space of a first imaging system that images the interventional medical device in a first imaging mode during the interventional medical procedure, based on identifying the shape of the optical shape sensing device. The instructions also cause the system to register the interventional medical device to the first coordinate space, identify the interventional medical device in a second coordinate space of a second imaging system that images the interventional medical device in a second imaging mode during the interventional medical procedure, and register the first coordinate space of the first imaging system to the second coordinate space of the second imaging system. The instructions further cause the system to segment the interventional medical device in the second coordinate space to obtain a segmented representation of the interventional medical device in the second coordinate space, register the interventional medical device to the second coordinate space using the segmented representation of the interventional medical device, and re-register the interventional medical device to the first coordinate space based on registering the interventional medical device to the second coordinate space.

According to yet another aspect of the present disclosure, a method for tracking location of an interventional medical device in an interventional medical procedure includes identifying a shape of the optical shape sensing device using optical shape sensing signals received via an interface from an optical shape sensing device which has a shape that conforms to a shape of the interventional medical device during the interventional medical procedure, and identifying the interventional medical device in a first coordinate space of a first imaging system that images the interventional medical device in a first imaging mode during the interventional medical procedure, based on identifying the shape of the optical shape sensing device. The method also includes registering the interventional medical device to the first coordinate space, identifying the interventional medical device in a second coordinate space of a second imaging system that images the interventional medical device in a second imaging mode during the interventional medical procedure, and registering the first coordinate space of the first imaging system to the second coordinate space of the second imaging system. The method further includes segmenting the interventional medical device in the second coordinate space to obtain a segmented representation of the interventional medical device in the second coordinate space, registering the interventional medical device to the second coordinate space using the segmented representation of the interventional medical device, and re-registering the interventional medical device to the first coordinate space based on registering the interventional medical device to the second coordinate space.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
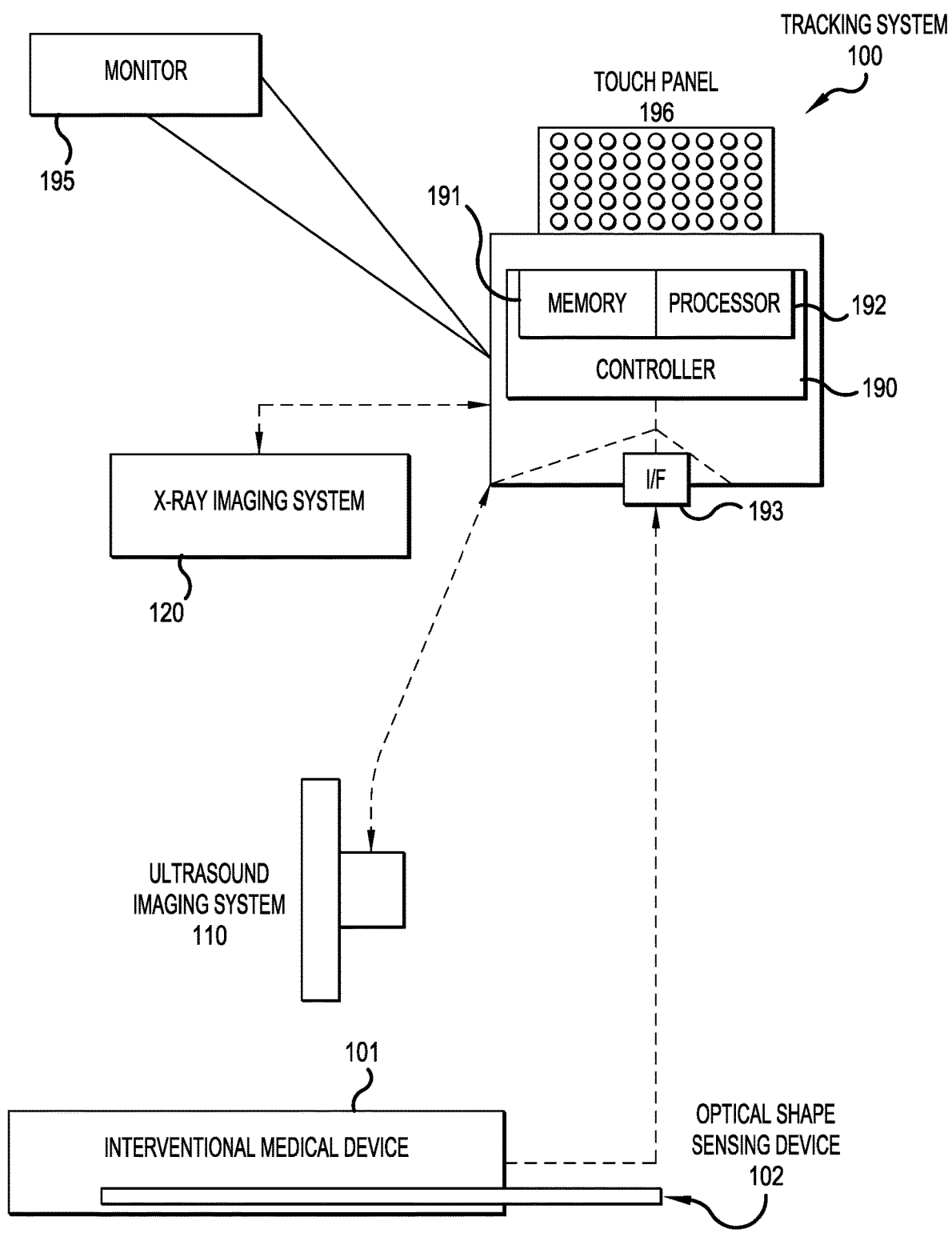
FIG. 1 illustrates a system for interventional medical device tracking, in accordance with a representative embodiment.

In the following detailed description, for the purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, interventional medical device tracking may leverage three-dimensional segmentation of interventional medical devices in an ultrasound volume and registration of an ultrasound imaging system to an X-Ray imaging system. Interventional medical device tracking may enable accurate maintenance of registration of an OSS device to both the ultrasound imaging system and the X-Ray imaging system throughout the duration of an interventional medical procedure and without repeating the X-Ray imaging.

As also described herein, use of the shape of an OSS device may enhance a process for identifying the OSS device in imagery such as from an ultrasound imaging system, and this in turn may enhance the registration processes described below.

FIG. 1 illustrates a system for interventional medical device tracking, in accordance with a representative embodiment.

FIG. 1 illustrates a tracking system 100. The tracking system 100 includes a console with a controller 190, an interface 193 and a touch panel 196. The controller 190 includes at least a memory 191 that stores instructions and a processor 192 that executes the instructions. The controller 190 controls one or more aspects of methods described herein. The processor 192 retrieves or otherwise receives instructions from the memory 191 via a bus (not shown). When executed by the processor 192, the instructions cause the controller 190 to implement one or more aspects of the methods shown in and described with respect to FIG. 5, FIG. 6, FIG. 7 and FIG. 8. The interface 193 provides an interface between the console that includes the controller 190 and an optical shape sensing device 102. The interface 193 is representative of interfaces between elements and components of the tracking system 100. The touch panel 196 includes buttons, keys and any other touch surfaces that can be used to input instructions from a user to the tracking system 100.

The tracking system 100 also includes a monitor 195, an X-Ray imaging system 120, and an ultrasound imaging system 110. The monitor 195 may be used to display images from the X-Ray imaging system 120 and the ultrasound imaging system 110. As a non-limiting example, the X-Ray imaging system 120 may perform fluoroscopic imaging during the interventional medical procedure. Also as a non-limiting example, the ultrasound imaging system 110 may perform transesophageal echocardiography (TEE) or other forms of ultrasound imaging. The X-Ray imaging system 120 performs imaging in a three-dimensional coordinate space that may be centered at an isocenter of a C-arm of the X-Ray imaging system 120. The ultrasound imaging system 110 performs imaging in another three-dimensional coordinate space. The three-dimensional coordinate space of the ultrasound imaging system 110 and other three-dimensional coordinate spaces may be registered to the three-dimensional coordinate space of the X-Ray imaging system 120 so that the isocenter of the C-arm of the X-Ray imaging system 120 becomes the origin of all such registered coordinate spaces.

The tracking system 100 also includes an interventional medical device 101 integrated with the optical shape sensing device 102. The optical shape sensing device 102 may be flexible and may have a shape that flexibly conforms to a shape of the interventional medical device 101 during the interventional medical procedure. In the descriptions herein, references to the interventional medical device 101 are also to the optical shape sensing device 102 insofar as the optical shape sensing device 102 is integrated with the interventional medical device 101. On the other hand, references to the optical shape sensing device 102 may be particular to the optical shape sensing device 102 independent of the interventional medical device 101 insofar as the optical shape sensing device 102 independently interfaces the controller 190 via the interface 193 to provide optical shape sensing signals generated by the optical shape sensing device 102.

The elements and components of the tracking system 100 in FIG. 1 may be provided together or may be distributed. For example, the controller 190, the monitor 195 and the touch panel 196 may be provided as an integrated computer system that is provided separately from the X-Ray imaging system 120, the ultrasound imaging system 110 and the interventional medical device 101. The X-Ray imaging system 120, the ultrasound imaging system 110 and the interventional medical device 101 may be provided separately from one another, and may be integrated together via an integrated computer system that includes the controller 190, the monitor 195 and the touch panel 196.

The controller 190 may include one or more input interface(s) in addition to the interface 193. The interface 193 and other input interfaces (not shown) of the controller 190 may include cables, adapters, ports, disk drives, antennas for wireless communications, and other forms of interfaces specifically used to connect elements and components of the tracking system 100. The input interfaces may further connect user interfaces, such as a mouse, a keyboard, a microphone, a video camera, a touchscreen display, or another element or component to the controller 190. The interfaces of the tracking system 100 may connect the controller 190 to the monitor 195, to the X-Ray imaging system 120, and to the ultrasound imaging system 110. For example, the controller 190 may be connected to the monitor 195 via a local wired interface such as an Ethernet cable or via a local wireless interface such as a Wi-Fi connection.

The monitor 195 may be a computer monitor, a display on a mobile device, a television, an electronic whiteboard, or another screen configured to display electronic imagery. The monitor 195 may also include one or more input interface(s) such as those noted above that may connect other elements or components to the monitor 195. The monitor 195 may also include a touch screen that enables direct input via touch.

In one set of embodiments, the tracking system 100 tracks the interventional medical device 101 during an interventional medical procedure. The X-Ray imaging system 120 may be a first imaging system that images the interventional medical device 101 during the interventional medical procedure, and the ultrasound imaging system 110 may be a second imaging system that images the interventional medical device 101 during the interventional medical procedure. When executed by the processor 192, the instructions stored in the memory 191 cause the tracking system 100 to track locations of the interventional medical device 101 during the interventional medical procedure. The process by which the interventional medical device 101 is tracked may include identifying a shape of the optical shape sensing device 102 using optical shape sensing signals received from the optical shape sensing device 102 via the interface 193. The process in this set of embodiments may also include identifying the interventional medical device 101 in a first coordinate space of the X-Ray imaging system 120, based on identifying the shape of the optical shape sensing device 102. The interventional medical device 101 is then registered to the first coordinate space of the X-Ray imaging system 120. The process may also include identifying the interventional medical device 101 in a second coordinate space of the ultrasound imaging system 110. The first coordinate space of the X-Ray imaging system 120 is registered to the second coordinate space of the ultrasound imaging system 110. The process of tracking location of the interventional medical device 101 in this set of embodiments may also include segmenting the interventional medical device 101 in the second coordinate space of the ultrasound imaging system 110 to obtain a segmented representation of the interventional medical device 101 in the second coordinate space. The interventional medical device 101 is then registered to the second coordinate space of the ultrasound imaging system 110 using the segmented representation of the interventional medical device. Afterwards, the interventional medical device 101 is re-registered to the first coordinate space of the X-Ray imaging system 120 based on registering the interventional medical device 101 to the second coordinate space using the segmented representation. The re-registration of the interventional medical device 101 to the first coordinate space of the X-Ray imaging system 120 is performed without requiring additional X-Ray imaging of the patient. The process performed in this set of operations may be performed on-demand, periodically, or once movement of the interventional medical device 101 beyond a threshold is detected.

The controller 190 may perform some of the operations described herein directly and may implement other operations described herein indirectly. For example, the controller 190 may directly control displays of the monitor 195, and indirectly control imaging by the X-Ray imaging system 120 and/or imaging by the ultrasound imaging system 110. Accordingly, the process implemented by the tracking system 100 when the processor 192 executes instructions from the memory 191 may include steps not directly performed by the controller 190.

In another set of embodiments using the tracking system 100, registration may be performed using a predetermined shape of the interventional medical device 101. For example, a predetermined shape of the interventional medical device 101 may be stored as a template in the memory 191 and retrieved from the memory 191 for use in searching the ultrasound space for the interventional medical device 101. A shape of the interventional medical device 101 may also be dynamically obtained from the optical shape sensing device 102. In this set of embodiments, the ultrasound imaging system 110 may be a first imaging system and the X-Ray imaging system 120 may be a second imaging system. The interventional medical device 101 may be registered to the ultrasound space (first coordinate space) based on the shape of the interventional medical device 101 identified using the optical shape sensing signals and based on the shape of the interventional medical device 101 identified in the ultrasound space (first coordinate space). A process for tracking the interventional medical device 101 may include identifying a shape of the optical shape sensing device 102 using optical shape sensing signals received from the optical shape sensing device 102 via the interface 193, and identifying a shape of the interventional medical device 101 in a first coordinate space of the ultrasound system (first imaging system) that images the interventional medical device 101 in a first imaging mode during the interventional medical procedure. The interventional medical device 101 is registered to the ultrasound space (first coordinate space) based on the shape of the interventional medical device 101 identified using the optical shape sensing signals and based on the shape of the interventional medical device 101 identified in the ultrasound space (first coordinate space). In this set of embodiments, preliminary registration of the X-Ray imaging system to the interventional medical device 101 and the ultrasound imaging system 110 is not required in order to register the interventional medical device 101 to the ultrasound imaging system 110 using the known shape of the interventional medical device 101.

Before proceeding to the description of FIG. 2A, the concepts of registration and segmentation will be more fully explained next. Registration involves aligning disparate three-dimensional coordinate systems. In FIG. 1, the X-Ray imaging system 120, the ultrasound imaging system 110 and the optical shape sensing device 102 may each have its own three-dimensional coordinate system. A common three-dimensional coordinate system is provided by aligning the disparate three-dimensional coordinate systems such as by sharing a common origin and set of axes. Registration may include first adjusting the origin of one coordinate system to the origin of another coordinate system, and then aligning axes of the one coordinate system to the axes of the other coordinate system. Registration typically involves calculating and applying transformation matrices based on observations of common three-dimensional elements in the two coordinate systems.

Segmentation produces a representation of the surface of structures such as anatomical features and the interventional medical device 101. The segmented representation consists for example of a set of points in three-dimensional (3-D) coordinates on the surfaces of the structure, and triangular plane segments defined by connecting neighboring groups of three points, such that the entire structure is covered by a mesh of non-intersecting triangular planes. A three-dimensional model of the interventional medical device 101 is obtained by segmenting. Segmenting may also involve performing segmentation on anatomy structures, and/or other structures present in a three-dimensional ultrasound volume.

Figure 2A:
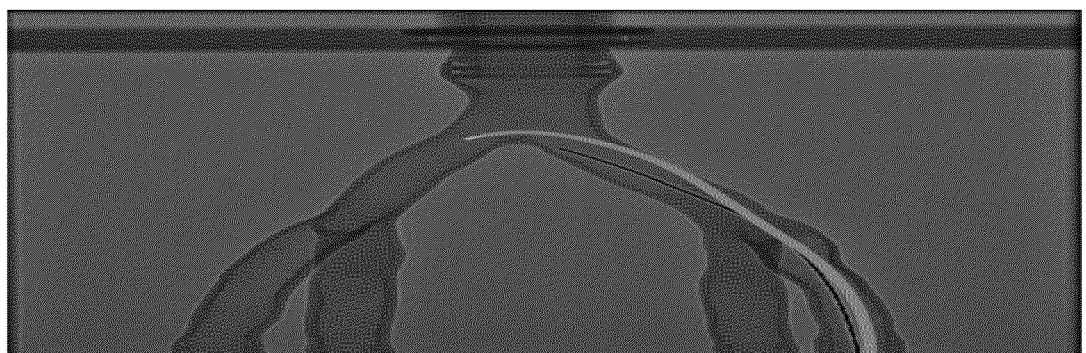
FIG. 2A illustrates registration of an interventional medical device to an X-Ray imaging system in interventional medical device tracking, in accordance with a representative embodiment.

FIG. 2A illustrates registration of an interventional medical device to an X-Ray imaging system in interventional medical device tracking, in accordance with a representative embodiment.

In FIG. 2A an optical fiber is integrated into an interventional medical device 201. An example of the optical fiber in FIG. 2A is the optical shape sensing device 102 in FIG. 1 The optical fiber provides the position and orientation of the interventional medical device 201. An example of the interventional medical device 201 in FIG. 2A is a catheter with a guidewire. In FIG. 2A, the optical fiber may be integrated into the interventional medical device 201 (e.g., into a guidewire of a catheter) in a vascular branch on the right side. The interventional medical device 201 with the integrated optical fiber is overlaid on an X-ray (fluoroscopy) image of a vascular phantom produced by the X-Ray imaging system 120.

In FIG. 2A, a shape of the optical fiber may be identified using optical shape sensing signals received from the optical fiber via an interface such as the interface 193. The X-Ray imaging system 120 may be a first imaging system that produces the X-ray image in a first coordinate space particular to the X-Ray imaging system 120. The interventional medical device 201 is registered to the X-Ray imaging system 120 by assigning locations of the interventional medical device 201 from the optical shape sensing signals to coordinates of the interventional medical device 201 in the first coordinate system based on the X-ray image. The interventional medical device 201 may be registered to the X-Ray coordinate space using two X-Ray projection images offset by 30 degrees or more. An operator identifies the tip of the interventional medical device 201 in each X-Ray image and the visible portion of the interventional medical device 201 is automatically detected. The transform from the interventional medical device 201 and the X-Ray coordinate space is determined from the two X-Ray projections and the reconstruction of the interventional medical device 201 based on the optical shape sensing signals from the optical fiber. The interventional medical device 201 is identified in the first coordinate space of the X-Ray imaging system 120 during the interventional medical procedure, based on identifying the shape of the optical shape sensing device 102 using the optical shape sensing signals from the optical fiber.

Figure 2B:
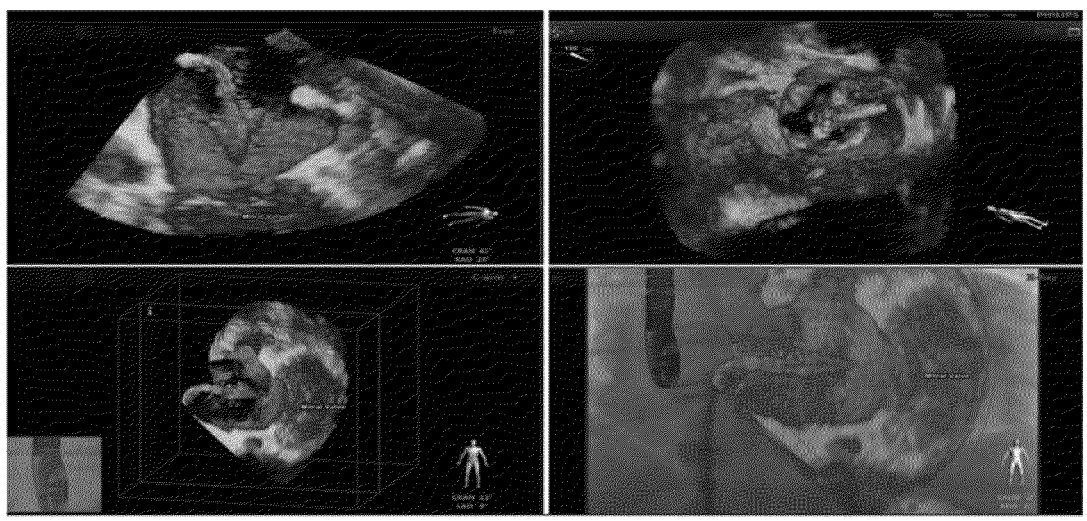
FIG. 2B illustrates registration of an ultrasound system to an X-Ray imaging system in interventional medical device tracking, in accordance with a representative embodiment.

FIG. 2B illustrates registration of an ultrasound system to an X-Ray imaging system 120 in interventional medical device tracking, in accordance with a representative embodiment.

In FIG. 2B, registration between the ultrasound imaging system 110 and the X-Ray imaging system 120 is accomplished through image fusion platforms. An example of an image fusion platform is EchoNavigator. A registration algorithm provided by EchoNavigator is based on taking a fluoroscopic image from the X-Ray imaging system 120. The fluoroscopic image contains the probe head of the ultrasound imaging system 110. As an example, the ultrasound imaging system 110 may be a transesophageal echocardiography (TEE) ultrasound system. From the pose of the probe head in the X-Ray image, the transform relating ultrasound space to X-Ray space ($T_{UX}$) can be calculated.

Figure 2C:
FIG. 2C illustrates registration of an interventional medical device to an ultrasound system in interventional medical device tracking, in accordance with a representative embodiment.

FIG. 2C illustrates registration of an interventional medical device to an ultrasound system in interventional medical device tracking, in accordance with a representative embodiment.

As shown in FIG. 2C, multiple registrations between different coordinate systems can be integrated so that three or more coordinate systems are aligned. In FIG. 2C, the optical shape sensing coordinate system (OSS Space) can be registered to the X-Ray imaging system coordinate system (X-Ray Space) using a program executed by the controller 190. The X-Ray imaging system coordinate system (X-Ray Space) can be registered to the local environment (Patient Space) which includes the X-Ray imaging system 120 using a program such as EchoNavigator executed by the controller 190. Separately, the ultrasound imaging system coordinate system (US Space) can be registered to the X-Ray imaging system coordinate system (X-Ray Space) using a program such as EchoNavigator executed by the controller 190.

Once the interventional medical device 101 and the ultrasound imaging system 110 have both been registered to the X-Ray space, the interventional medical device 101 can be rendered in the ultrasound imaging system coordinate system (US Space) via transforms outlined in FIG. 2C.

Figure 3:
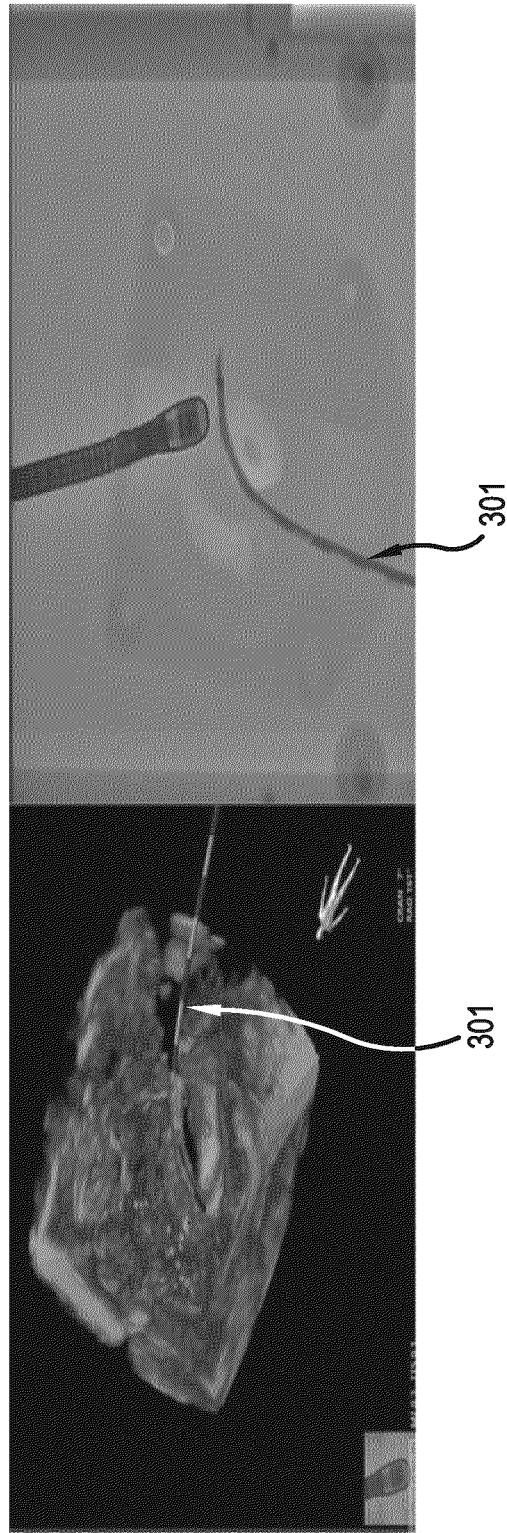
FIG. 3 illustrates registrations of an interventional medical device to an ultrasound system and to a X-Ray system in interventional medical device tracking, in accordance with another representative embodiment.

FIG. 3 illustrates registrations of an interventional medical device to an ultrasound system and to a X-Ray system in interventional medical device tracking, in accordance with another representative embodiment.

In FIG. 3, a guidewire 301 is shown in the ultrasound space on the left and in the X-Ray space on the right. Since the interventional medical device 101 is registered to the ultrasound space and to the X-Ray space, and the ultrasound space is registered to the X-Ray space, the images shown in FIG. 3 reflect the same coordinate system even though the perspective differs between the two images.

Figure 4:
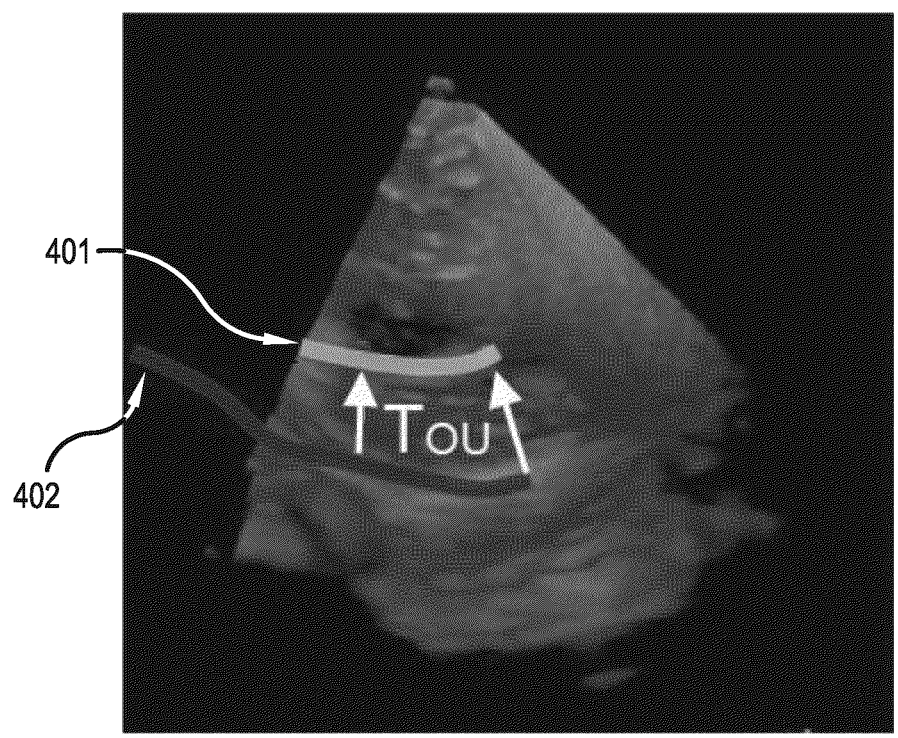
FIG. 4 illustrates registration of an interventional medical device to an ultrasound system in interventional medical device tracking, in accordance with a representative embodiment.

FIG. 4 illustrates registration of an interventional medical device to an ultrasound system in interventional medical device tracking, in accordance with a representative embodiment.

In FIG. 4, reconstruction of the interventional medical device 101 from the optical shape sensing using the optical shape sensing device 102 is shown as the OSS reconstruction 402. The image-based segmentation of the optical shape sensing device 102 in the ultrasound space is shown as the segmented representation 401. As shown, in the registration process described herein, the OSS reconstruction 402 can be registered to the segmented representation 401 in the ultrasound space. Transformation $T_{OU}$ relates the current location of the OSS reconstruction 402 to the segmented representation 401 of the interventional medical device 101 location in ultrasound space.

In a first set of embodiments described herein, registration may be accomplished by identifying a location of an interventional medical device 101 in medical imagery such as by user-designation, tracking of a sensor integrated to a tip of the interventional medical device 101, or otherwise. Three-dimensional segmentation of the interventional medical device 101 in ultrasound imagery may be used to update the registration in the first set of embodiments. Three-dimensional segmentation of tube-like interventional medical devices in ultrasound may be achieved through image processing techniques combined with sensor tracking technology. Examples of three-dimensional segmentation of interventional medical devices are explained in U.S. Provisional Patent Application No. 62/855,013, filed in the U.S. Patent and Trademark Office on May 31, 2019, the disclosure of which is incorporated by reference in its entirety. Examples of tube-like interventional medical devices that are readily subject to three-dimensional segmentation include guidewires and catheters. Alternative mechanisms for identifying the interventional medical devices in the ultrasound images include initializations by users clicking on the locations of the tips of the interventional medical devices in the ultrasound images, as well as by deep learning using artificial intelligence based on previous instantiations of identifications of interventional medical devices in ultrasound images.

The updated registrations address errors known to occur when optical shape sensing is registered to X-Ray space and/or ultrasound space. That is, while optical shape sensing provides highly accurate reconstructions of the local shape of an interventional medical device 101, optical shape sensing may be prone to errors in registration offset due to the accumulation of error along the length of the interventional medical device 101. For example, while the accuracy may be very good immediately after registration of the interventional medical device 101 to the X-Ray space is completed, if the proximal end of the interventional medical device 101 is moved several centimeters, the registration may accumulate a noticeable error. Using the teachings of the first set of embodiments provided herein, the error can be corrected by re-registration without requiring additional exposures to X-Ray projections, and thus without increasing the X-Ray dose exposure to the patient and clinicians. Moreover, registration of the interventional medical device 101 to the X-Ray imaging system 120 can be updated continually, on-demand of the clinician (e.g., when the clinician notices an error) or automatically (e.g., when the tracking system 100 detects that misalignment exceeds a predetermined threshold). By leveraging segmentation of the interventional medical device 101 in the ultrasound space, and registrations as described herein, the registration of the interventional medical device 101 can be continually and accurately updated throughout the duration of the procedure.

The interventional medical device 101, which has been roughly registered to X-Ray space and three-dimensional ultrasound space, can maintain an automatically fine-tuned registration based on the segmented shape of the interventional medical device 101 in three-dimensional ultrasound. The shape of the interventional medical device 101 in three-dimensional ultrasound is determined via image processing or deep learning techniques. A rigid point-to-point transform is then calculated from the corresponding portion of the interventional medical device 101 to the three-dimensional segmentation of the interventional medical device 101 in the ultrasound coordinate system. Accurate registration of the interventional medical device 101 can be maintained throughout the procedure by automatically segmenting the interventional medical device 101 in the image and aligning the reconstruction from the optical shape sensing device 102.

In a second set of embodiments, registration of an interventional medical device 101 may be achieved and updated using a known shape of the interventional medical device 101, and this may involve a simplified workflow compared to the first set of embodiments. For example, when a shape of the interventional medical device 101 is known, such as from a template and/or from the optical shape sensing device 102, the shape can be identified in the ultrasound coordinate space, and the registration between optical shape sensing and the ultrasound space can be achieved without first registering the interventional medical device 101 to the X-Ray imaging system 120. A template of the shape of the interventional medical device 101 may be obtained from a library of templates stored in a memory such as the memory 191. The template may include a template of a portion of the shape of the interventional medical device 101, such as a template of the shape of a distal tip of the interventional medical device 101. When the template is a template of a portion of the shape, the remainder of the shape of the interventional medical device 101 may be identified based on image analysis software searching for the remainder of the shape of the interventional medical device 101 in areas proximate to the portion of the shape identified in ultrasound imagery from the template of the portion of the shape.

Additionally, in the second set of embodiments, registration between the ultrasound coordinate space and the X-Ray coordinate space may be performed without requiring an X-Ray image of the probe head of the ultrasound imaging system 110. For example, the common shape of the interventional medical device 101 in both coordinate systems may be used as the mechanism to register the two coordinate systems. When the interventional medical device 101 is already registered to the X-Ray space, and the interventional medical device 101 may be registered to the ultrasound space using a template of the shape of the interventional medical device 101, then the ultrasound coordinate system may be registered to the X-Ray coordinate system by calculating the transformation from the segmentation of the interventional medical device 101 in the ultrasound space to the corresponding interventional medical device 101 in the X-Ray space.

In the second set of embodiments, the portion of the shape may be used as a constraint in an initial search for the shape of the interventional medical device 101 in the ultrasound imagery. Artificial intelligence may be applied to analyze the ultrasound imagery in the ultrasound coordinate space. The search may be initially constrained by the tip of the interventional medical device 101, and once the tip of the interventional medical device 101 is identified in the search, artificial intelligence may be applied to find the remainder of the shape of the interventional medical device 101 based on characteristics and parameters identified from previous instantiations of the interventional medical device 101 in previous searches of ultrasound imagery.

In both the first set of embodiments and the second set of embodiments, metrics may be generated to show a correlation between identifications of the interventional medical device 101 in different coordinate spaces. For example, a metric may be generated based on a correlation between an existing location of the segmented representation of the interventional medical device 101 in the ultrasound space and a newly-identified location of the interventional medical device 101 in the ultrasound coordinates. The correlation may be an estimate of confidence as to the accuracy of the identification, and may be based on, for example, a quantity of discrepancies between the segmented representation and the proposed newly-identified locations of the interventional medical device 101 in the ultrasound coordinates.

Figure 5:
FIG. 5 illustrates a method for interventional medical device tracking, in accordance with a representative embodiment.

FIG. 5 illustrates a method for interventional medical device tracking, in accordance with a representative embodiment.

In FIG. 5, the method starts at S510 by identifying a shape of an optical shape sensing device. The optical shape sensing device may be the optical shape sensing device 102 in the embodiment of FIG. 1, and may comprise an optical fiber. The optical shape sensing device may be identified using optical shape sensing technology described above.

At S520, the method of FIG. 5 includes identifying an interventional medical device in a first coordinate space. The first coordinate space may be the coordinate space of a first imaging system operating in a first imaging mode, such as of the X-Ray imaging system 120 operating in an X-Ray imaging mode. The identification at S520 may be by a user designating the interventional medical device 101 in an X-Ray image, or by image analysis software identifying the interventional medical device 101 in an X-Ray image.

At S530, the method of FIG. 5 includes registering the interventional medical device 101 to the first coordinate space. The registration at S530 may be of the interventional medical device 101 to the X-Ray space of the X-Ray imaging system 120. The registration at S530 may be based on the shape of the interventional medical device 101 identified at S510 from the conforming shape of the optical shape sensing device 102. The registration at S520 may also be based on the shape of the interventional medical device 101 identified at S520 from the X-Ray image.

At S540, the method of FIG. 5 includes identifying the interventional medical device 101 in a second coordinate space. The second coordinate space may be the coordinate space of a second imaging system operating in a second imaging mode, such as of the ultrasound imaging system 110 operating in an ultrasound imaging mode. The identification at S540 may be by a user designating the interventional medical device 101 in an ultrasound image, or by image analysis software identifying the interventional medical device 01 in an ultrasound image. Although not shown in FIG. 5, S540 may be performed between S550 and S560 (described below), so as to register the first coordinate space to the second coordinate space before fine-tuning the registration of the interventional medical device 101 in the second coordinate space (i.e., in the ultrasound space).

In an embodiment, a user may identify a tip of the interventional medical device 101 in an ultrasound image, and image analysis software may constrain a search for the remainder of the interventional medical device 101 to the area around the designated tip.

In another embodiment, a sensor on the tip of the interventional medical device 101 may be a passive ultrasound sensor that responds to emissions from the ultrasound imaging system 110. Sensor-based tracking of an interventional medical device 101 is described in U.S. Provisional Patent Application No. 62/855,013, filed in the U.S. Patent and Trademark Office on May 31, 2019, the disclosure of which is incorporated by reference in its entirety.

In the embodiment using the sensor on the tip of the interventional medical device 101, image analysis software may constrain a search for the remainder of the interventional medical device 101 to the area around the tip identified from a signal from the sensor. The constraint may be based on identification of the tip of the interventional medical device 101 by a user, identification based on a signal from a passive ultrasound sensor, or identification from image analysis software that is trained by artificial intelligence to recognize the tip of the interventional medical device.

In another embodiment, the interventional medical device 101 may be roughly registered to the ultrasound space via the $T_{OX}$ transform from the interventional medical device 101 to the X-Ray space and via the $T_{UX}$ transform from the ultrasound space to the X-Ray space. The ultrasound image-based device segmentation described below at S560 is then continually calculated throughout the acquisition, using the tip of the interventional medical device 101 as a rough estimate to constrain the search space of the image processing algorithm. The transform $T_{OU}$ from the interventional medical device 101 to the ultrasound space may be calculated on each ultrasound frame, and the registration of the interventional medical device 101 to the ultrasound space is updated continuously or at fixed intervals throughout the procedure.

At S550, the first coordinate space is registered to the second coordinate space. Registration at S550 may be performed by imaging a head of an ultrasound probe in the ultrasound imaging system 110 using the X-Ray imaging system 120. As noted above, in some embodiments, S550 may be performed before S540.

At S560, the interventional medical device in the second coordinate space is segmented to produce a segmented representation of the interventional medical device. In an embodiment, the segmentation at S560 is initialized by a user identifying the interventional medical device 101 in an ultrasound image at S540. An image-processing algorithm searches for the interventional medical device 101 in the image in the region identified by the user. A rigid transform $T_{OU}$ from the interventional medical device 101 to the ultrasound space is calculated such that the distal portion of the interventional medical device 101 corresponding to the length of the ultrasound device segmentation is rotated/translated to most closely match the segmented representation in ultrasound. The rigid transform $T_{OU}$ is then applied to the entire length of the reconstruction from the optical shape sensing device 102.

At S565, the segmented representation of the interventional medical device 101 is rendered, such as on the monitor 195 in FIG. 1. The segmented representation of the interventional medical device 101 may be overlaid on an ultrasound image that, in turn, is overlaid on an X-Ray image.

At S570, the interventional medical device is registered to the second coordinate space of the ultrasound imaging system 110. The registration at S570 may be the initial registration of the interventional medical device 101 to the ultrasound space, or may be a repeated registration of the interventional medical device 101 to correct an earlier registration that has become outdated.

At S580, the interventional medical device 101 is re-registered to the first coordinate space of the X-Ray imaging system 120. The re-registration at S580 may correct an outdated earlier registration, and does not require additional imaging by the X-Ray imaging system 120.

In an embodiment, the interventional medical device 101 is segmented in the ultrasound volume based on artificial intelligence from previous identifications of the interventional medical device 101 in ultrasound images. In this embodiment, initialization from a user identification or from a sensor is not necessarily required to constrain the search space. The transform $T_{OU}$ from the interventional medical device 101 to the ultrasound space may be calculated on each ultrasound frame and the registration from the interventional medical device 101 to the ultrasound space is continuously updated throughout the procedure.

Although not shown in FIG. 5, the first coordinate space may be re-registered to the second coordinate space by calculating the transformation from the segmented representation of the interventional medical device 101 in the first coordinate space to a shape of the interventional medical device 101 identified based on optical shape sensing in the second coordinate system. According to the second set of embodiments described herein, the re-registration may be performed without requiring an X-Ray image of the probe head of the ultrasound imaging system 110. When the interventional medical device 101 is already registered to the X-Ray space and the interventional medical device 101 is already registered to any ultrasound space based on the template of the shape, the ultrasound space may be registered to the X-Ray space by calculating the transformation from the segmented representation of the interventional medical device 101 in the ultrasound space to the corresponding section of the interventional medical device 101 in the X-Ray space.

Figure 6:
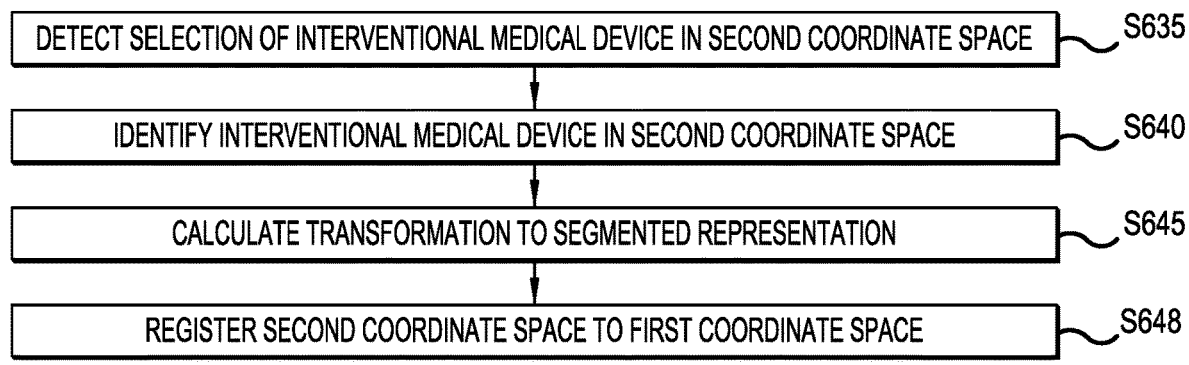
FIG. 6 illustrates a method for interventional medical device tracking, in accordance with a representative embodiment.

FIG. 6 illustrates a method for interventional medical device tracking, in accordance with a representative embodiment.

In the method of FIG. 6, a selection of an interventional medical device 101 is detected in the second coordinate space of the ultrasound imaging system 110. The selection may be a user selection of a tip of the interventional medical device 101.

At S640, the interventional medical device 101 is identified in the second coordinate space. The identification at S640 is based on the selection at S635, and may involve using image analysis software to search the area around where the user selects for the remainder of the interventional medical device 101.

At S645, the transform $T_{OU}$ from the existing location of the interventional medical device 101 to the segmented representation is calculated. Using the new $T_{OU}$ transform, the previous location of the interventional medical device 101 in the ultrasound space can be updated to the new location of the segmented representation.

At S648, the second coordinate space of the ultrasound imaging system 110 is registered to the first coordinate space of the X-Ray imaging system based on the segmented representation of the interventional medical device 101 in the second coordinate space of the ultrasound imaging system 110. By this registration, the previous location of the interventional medical device 101 in the X-Ray space is updated to account for any error due, for example, to movement of the interventional medical device 101.

The embodiment of FIG. 6 may be supplemental to the embodiment of FIG. 5, and includes functions that supplement the functions described with respect to FIG. 5.

In the description of the embodiment of FIG. 6 above, identification of the interventional medical device 101 in the ultrasound space is based on user designation of a tip of the interventional medical device 101. In another embodiment, a known shape of the interventional medical device 101 can be searched in the ultrasound space without requiring knowledge of the shape of the distal tip of the interventional medical device 101. A search for the known shape of the interventional medical device 101 may be based on information from optical shape sensing signals from the optical shape sensing device 102, and eliminates a need for a rough registration of the interventional medical device 101 to the ultrasound space via the transform $T_{OU}$.

Figure 7:
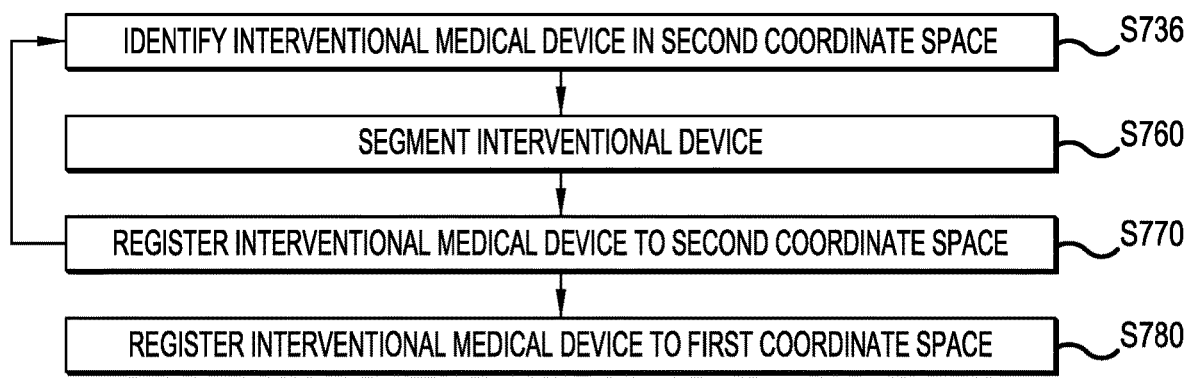
FIG. 7 illustrates a method for interventional medical device tracking, in accordance with a representative embodiment.

FIG. 7 illustrates a method for interventional medical device tracking, in accordance with a representative embodiment.

In FIG. 7, the interventional medical device 101 is identified in the second coordinate space of the ultrasound imaging system 110 at S736. The identification at S736 may be based on the user selecting a location of the tip of the interventional medical device 101 or by a signal from a passive ultrasound sensor on the tip of the interventional medical device 101.

At S760, the interventional medical device 101 is segmented in the ultrasound image to produce a segmented representation of the interventional medical device 101.

At S770, the interventional medical device 101 is registered to the second coordinate space of the ultrasound imaging system 110. The registration at S770 may be based on at least the transform $T_{OU}$.

At S780, the interventional medical device is registered to the first coordinate space of the X-Ray imaging system 120. The transform at S780 may be based on all three of the transforms $T_{OX}$, $T_{UX}$ and $T_{OU}$.

The embodiment of FIG. 7 may be supplemental to the embodiment of FIG. 5, and includes functions that supplement the functions described with respect to FIG. 5.

In the description of the embodiment of FIG. 7 above, identification of the interventional medical device 101 in the ultrasound space is based on user or sensor identification of a tip of the interventional medical device 101. In another embodiment, a known shape of the interventional medical device 101 can be retrieved from a template or from the information from optical shape sensing signals from the optical shape sensing device 102. Registration based on a template or knowledge of the shape of the interventional medical device 101 can be used to define or maintain the registration between the ultrasound space and the X-Ray space, particularly if the ultrasound probe of the ultrasound imaging system 110 is at an angle that is difficult to detect in the X-Ray imaging system 120. Assuming the transform $T_{OU}$ from the interventional medical device 101 to the ultrasound space is known and the transform $T_{OX}$ from the interventional medical device 101 to the X-Ray space is known, the transform $T_{UX}$ from ultrasound space to the X-Ray space can be determined, loosely, as ($T_{UX}$=inv($T_{OU}$) *$T_{OX}$). As in other embodiments described herein, an embodiment which maintains a registration by repeatedly updating the transform $T_{UX}$ may not require additional exposures to X-Rays.

Figure 8:
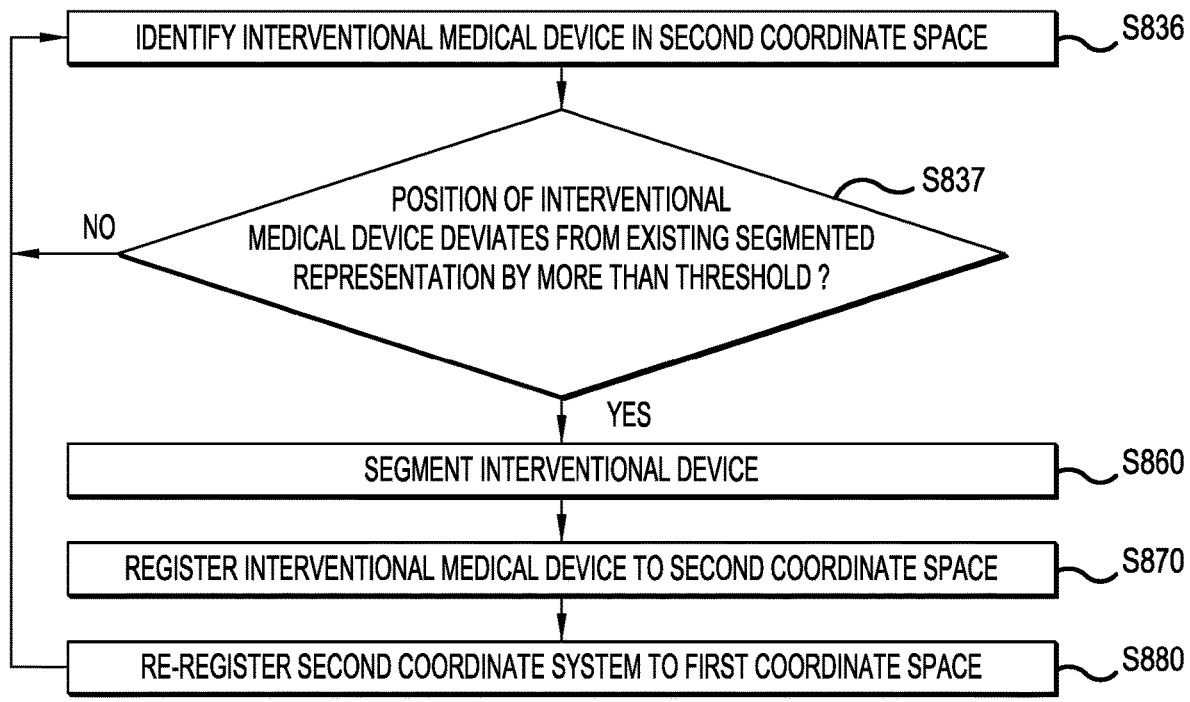
FIG. 8 illustrates a method for interventional medical device tracking, in accordance with a representative embodiment.

FIG. 8 illustrates a method for interventional medical device tracking, in accordance with a representative embodiment.

In FIG. 8, the method starts at S836 by identifying the interventional medical device 101 in the second coordinate space. The identification may be made based on a user designation or based on a signal from a sensor on the tip of the interventional medical device 101. The identification at S836 may also be made on-demand, periodically on a continuous basis during the interventional medical procedure, or based on detection of movement of the interventional medical device 101 compared to a previous registration.

At S837, a determination is made whether a position of the interventional medical device deviates from an existing segmented representation by more than a threshold. The determination at S837 may be based on detection of movement of the interventional medical device 101 compared to a previous registration. If any deviation does not exceed a threshold (S837=No), the method returns to S836, and otherwise proceeds to S860.

At S860, the interventional medical device 101 is segmented in the ultrasound space.

At S870, the interventional medical device 101 is registered to the second coordinate space based on the segmentation at S860.

At S880, the second coordinate system is re-registered to the first coordinate system. The re-registration at S880 is provided without requiring another exposure to X-Rays from the X-Ray imaging system 120.

After S880, the process returns to S836. Accordingly, the process of FIG. 8 is recursive, and may involve repeatedly checking whether a position of the interventional medical device 101 deviates from the last existing segmented representation by more than a threshold and correcting the deviation by updating registrations of the interventional medical device 101 to the X-Ray space and the ultrasound space.

The embodiment of FIG. 8 may be supplemental to the embodiment of FIG. 5, and includes functions that supplement the functions described with respect to FIG. 5.

In the description of the embodiment of FIG. 8 above, identification of the interventional medical device 101 in the ultrasound space is again based on knowledge of the tip of the interventional medical device 101. In another embodiment, irregularly-shaped therapeutic devices deployed with optical shape sensing may be delivered via a an OSS-enabled delivery sheath or catheter. A therapeutic device of known irregular shape may be detected in the ultrasound space via image-based segmentation or via artificial analysis applied to previous instantiations of identifications of the OSS delivery sheath or catheter. Segmentation of the irregularly shaped therapeutic device may be used to locate the distal end of the OSS-enabled delivery device in ultrasound for repeated updating of the registration between the interventional medical device 101 and the ultrasound space.

In additional embodiments, registration methods described above may be triggered automatically. For example, an interventional medical device 101 may be continually segmented in ultrasound space in background processing. The existing registration of the interventional medical device 101 may be updated to most closely match the interventional medical device 101 in ultrasound space on every frame, on every nth frame, or only when a metric describing the correlation and/or offset between the location of the interventional medical device 101 and the location of the segmented representation of the interventional medical device 101 in ultrasound space exceeds a predetermined threshold.

Additionally, registration methods described above may be triggered on-demand. A user interface may include a metric describing the correlation and/or offset between the location of the interventional medical device 101 and the location of the interventional medical device 101 in ultrasound space. The user may then select an "update registration" soft button when the offset metric exceeds the desired error limit, or anytime the user wishes to update the current registration based on visual inspection.

Furthermore, a user interface may provide a metric describing success of registration after the registration has been performed. The metric may contain information about the correlation between the shape of the interventional medical device 101 in the re-registration and the shape of the interventional medical device 101 in the segmented representation in the ultrasound space. Alternatively, the metric may include a confidence level that the correct shape of the interventional medical device 101 has been detected.

Figure 9:
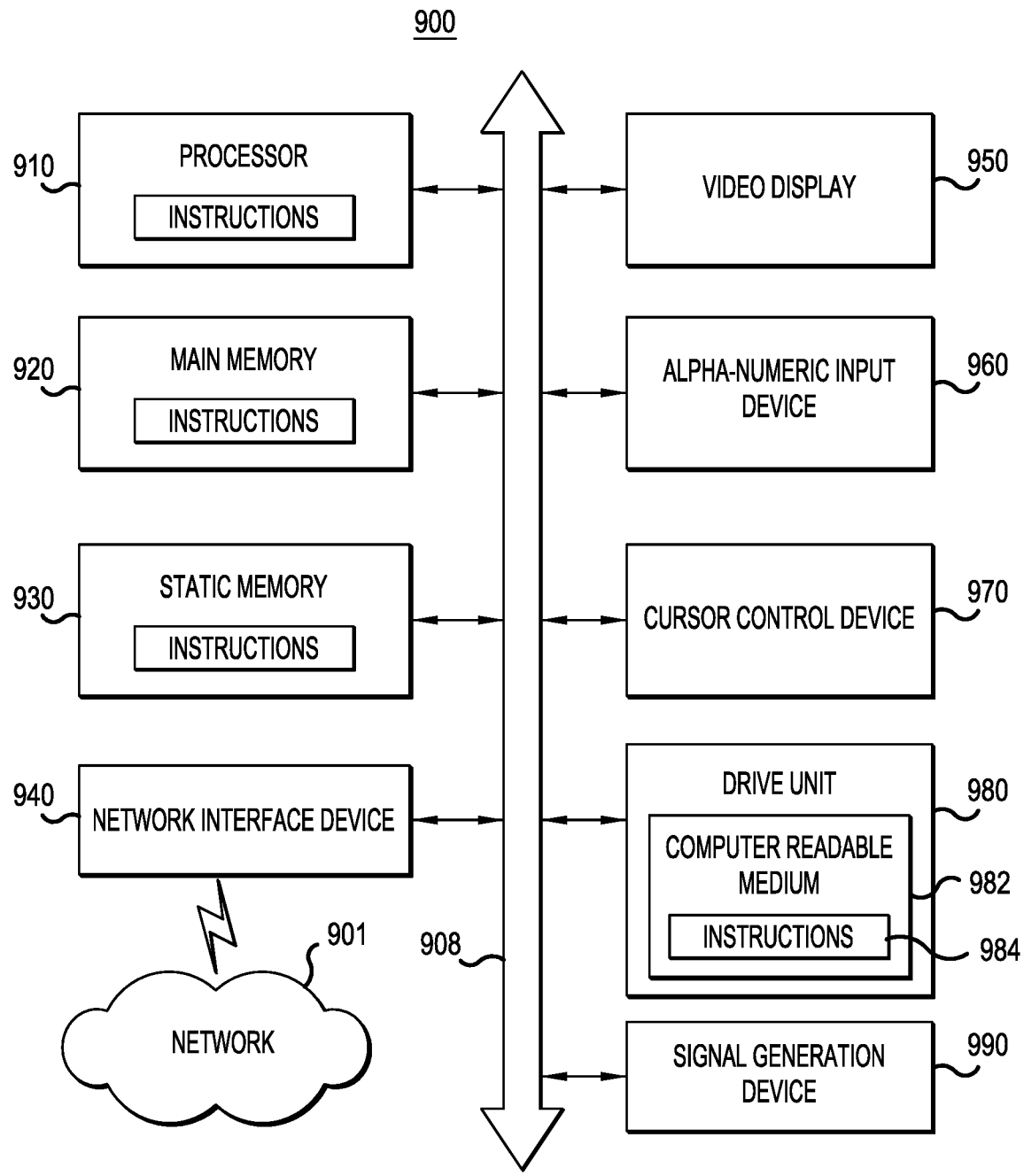
FIG. 9 illustrates a computer system, on which a method for interventional medical device tracking is implemented, in accordance with another representative embodiment.

FIG. 9 illustrates a computer system, on which a method for interventional medical device tracking is implemented, in accordance with some representative embodiments.

The computer system 900 of FIG. 9 shows a complete set of components for a communications device or a computer device. However, a "controller" as described herein may be implemented with less than the set of components of FIG. 9, such as by a memory and processor combination. The computer system 900 may include some or all elements of one or more component apparatuses in a system for interventional medical device tracking herein, although any such apparatus may not necessarily include one or more of the elements described for the computer system 900 and may include other elements not described.

Referring to FIG. 9, the computer system 900 includes a set of software instructions that can be executed to cause the computer system 900 to perform any of the methods or computer-based functions disclosed herein. The computer system 900 may operate as a standalone device or may be connected, for example, using a network 901, to other computer systems or peripheral devices. In embodiments, a computer system 900 performs logical processing based on digital signals received via an analog-to-digital converter.

In a networked deployment, the computer system 900 operates in the capacity of a server or as a client user computer in a server-client user network environment, or as a peer computer system in a peer-to-peer (or distributed) network environment. The computer system 900 can also be implemented as or incorporated into various devices, such as the controller 190 in FIG. 1A, a stationary computer, a mobile computer, a personal computer (PC), a laptop computer, a tablet computer, or any other machine capable of executing a set of software instructions (sequential or otherwise) that specify actions to be taken by that machine. The computer system 900 can be incorporated as or in a device that in turn is in an integrated system that includes additional devices. In an embodiment, the computer system 900 can be implemented using electronic devices that provide voice, video or data communication. Further, while the computer system 900 is illustrated in the singular, the term "system" shall also be taken to include any collection of systems or sub-systems that individually or jointly execute a set, or multiple sets, of software instructions to perform one or more computer functions.

As illustrated in FIG. 9, the computer system 900 includes a processor 910. The processor 910 may be considered a representative example of the processor 192 of the controller 190 in FIG. 1 and executes instructions to implement some or all aspects of methods and processes described herein. The processor 910 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The processor 910 is an article of manufacture and/or a machine component. The processor 910 is configured to execute software instructions to perform functions as described in the various embodiments herein. The processor 910 may be a general-purpose processor or may be part of an application specific integrated circuit (ASIC). The processor 910 may also be a microprocessor, a microcomputer, a processor chip, a controller, a microcontroller, a digital signal processor (DSP), a state machine, or a programmable logic device. The processor 910 may also be a logical circuit, including a programmable gate array (PGA), such as a field programmable gate array (FPGA), or another type of circuit that includes discrete gate and/or transistor logic. The processor 910 may be a central processing unit (CPU), a graphics processing unit (GPU), or both. Additionally, any processor described herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems. The term computing device should also be interpreted to include a collection or network of computing devices each including a processor or processors. Programs have software instructions performed by one or multiple processors that may be within the same computing device or which may be distributed across multiple computing devices.

The computer system 900 further includes a main memory 920 and a static memory 930, where memories in the computer system 900 communicate with each other and the processor 910 via a bus 908. Either or both of the main memory 920 and the static memory 930 may be considered representative examples of the memory 191 of the controller 190 in FIG. 1B, and store instructions used to implement some or all aspects of methods and processes described herein. Memories described herein are tangible storage mediums for storing data and executable software instructions and are non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The main memory 920 and the static memory 930 are articles of manufacture and/or machine components. The main memory 920 and the static memory 930 are computer-readable mediums from which data and executable software instructions can be read by a computer (e.g., the processor 910). Each of the main memory 920 and the static memory 930 may be implemented as one or more of random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. The memories may be volatile or non-volatile, secure and/or encrypted, unsecure and/or unencrypted.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

As shown, the computer system 900 further includes a video display unit 950, such as a liquid crystal display (LCD), an organic light emitting diode (OLED), a flat panel display, a solid-state display, or a cathode ray tube (CRT), for example. Additionally, the computer system 900 includes an input device 960, such as a keyboard/virtual keyboard or touch-sensitive input screen or speech input with speech recognition, and a cursor control device 970, such as a mouse or touch-sensitive input screen or pad. The computer system 900 also optionally includes a disk drive unit 980, a signal generation device 990, such as a speaker or remote control, and/or a network interface device 940.

In an embodiment, as depicted in FIG. 9, the disk drive unit 980 includes a computer-readable medium 982 in which one or more sets of software instructions 984 (software) are embedded. The sets of software instructions 984 are read from the computer-readable medium 982 to be executed by the processor 910. Further, the software instructions 984, when executed by the processor 910, perform one or more steps of the methods and processes as described herein. In an embodiment, the software instructions 984 reside all or in part within the main memory 920, the static memory 930 and/or the processor 910 during execution by the computer system 900. Further, the computer-readable medium 982 may include software instructions 984 or receive and execute software instructions 984 responsive to a propagated signal, so that a device connected to a network 901 communicates voice, video or data over the network 901. The software instructions 984 may be transmitted or received over the network 901 via the network interface device 940.

In an embodiment, dedicated hardware implementations, such as application-specific integrated circuits (ASICs), field programmable gate arrays (FPGAs), programmable logic arrays and other hardware components, are constructed to implement one or more of the methods described herein.

One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

Accordingly, interventional medical device tracking enables updated registrations to correct locations of an interventional medical device 101. Nevertheless, interventional medical device tracking is not limited as an application to specific details described herein, and instead is applicable to additional embodiments in which other types of medical imaging systems and interventional medical devices are used.

Although interventional medical device tracking has been described with reference to several exemplary embodiments, it is understood that the words that have been used are words of description and illustration, rather than words of limitation. Changes may be made within the purview of the appended claims, as presently stated and as amended, without departing from the scope and spirit of interventional medical device tracking in its aspects. Although interventional medical device tracking has been described with reference to particular means, materials and embodiments, interventional medical device tracking is not intended to be limited to the particulars disclosed; rather interventional medical device tracking extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

We claim:

1. A system for tracking location of an interventional medical device in an interventional medical procedure, comprising:
    an interface to an optical shape sensing device which has a shape that conforms to a shape of the interventional medical device during the interventional medical procedure; and
    a controller comprising a memory that stores instructions and a processor that executes the instructions, wherein, when executed by the processor, the instructions cause the system to:
    identify the shape of the optical shape sensing device using optical shape sensing signals received from the optical shape sensing device via the interface;
    identify the interventional medical device in a first coordinate space of a first imaging system that images the interventional medical device in a first imaging mode during the interventional medical procedure, based on identifying the shape of the optical shape sensing device;
    register the interventional medical device to the first coordinate space;
    identify the interventional medical device in a second coordinate space of a second imaging system that images the interventional medical device in a second imaging mode during the interventional medical procedure;
    register the first coordinate space of the first imaging system to the second coordinate space of the second imaging system;
    segment the interventional medical device in the second coordinate space to obtain a segmented representation of the interventional medical device in the second coordinate space;
    register the interventional medical device to the second coordinate space using the segmented representation of the interventional medical device; and
    re-register the interventional medical device to the first coordinate space based on registering the interventional medical device to the second coordinate space.

2. The system of claim 1, further comprising:
    the optical shape sensing device;
    an x-ray imaging system that comprises the first imaging system; and
    an ultrasound imaging system that comprises the second imaging system,
    wherein the instructions further cause the system to:
    render the segmented representation of the interventional medical device in the second coordinate space.

3. The system of claim 1, wherein the instructions further cause the system to:
    calculate a transform from the interventional medical device identified in the second coordinate space to the segmented representation of the interventional medical device in the second coordinate space, and
    register the second coordinate space to the first coordinate space based on the transform.

4. The system of claim 3, wherein the instructions further cause the system to:
    detect a selection of the interventional medical device in an image from the second imaging system, and search for the interventional medical device in a region of the image proximate to the selection, and
    wherein the transform is calculated by translating a distal portion of the interventional medical device in the image to match a corresponding distal portion of the interventional medical device in the segmentation.

5. The system of claim 3, wherein the instructions further cause the system to:
    repeatedly identify the interventional medical device in an image in the second coordinate space of the system using a tip of the interventional medical device as a constraint in a search of the image;
    segment the interventional medical device for each frame of imaging in the second imaging mode; and
    repeatedly register the interventional medical device to the second coordinate space.

6. The system of claim 1, wherein the instructions further cause the system to:
    repeatedly identify the interventional medical device in an image in the second coordinate space of the system;
    determine when a position of the interventional medical device deviates from the segmented representation of the interventional medical device in the first coordinate space by more than a predetermined threshold;
    re-segment the interventional medical device when the position of the interventional medical device deviates by more than the predetermined threshold; and
    re-register the interventional medical device to the second coordinate space and re-register the second coordinate space to the first coordinate system when the position of the interventional medical device deviates by more than the predetermined threshold.

7. A tangible non-transitory computer readable storage medium that stores a computer program, the computer program, when executed by a processor, causing a system that includes the tangible non-transitory computer readable storage medium to:
  identify, using optical shape sensing signals received via an interface, a shape of an optical shape sensing device which has a shape that conforms to a shape of an interventional medical device during an interventional medical procedure;
  identify the interventional medical device in a first coordinate space of a first imaging system that images the interventional medical device in a first imaging mode during the interventional medical procedure, based on identifying the shape of the optical shape sensing device;
  register the interventional medical device to the first coordinate space;
  identify the interventional medical device in a second coordinate space of a second imaging system that images the interventional medical device in a second imaging mode during the interventional medical procedure;
  register the first coordinate space of the first imaging system to the second coordinate space of the second imaging system;
  segment the interventional medical device in the second coordinate space to obtain a segmented representation of the interventional medical device in the second coordinate space;
  register the interventional medical device to the second coordinate space using the segmented representation of the interventional medical device; and
  re-register the interventional medical device to the first coordinate space based on registering the interventional medical device to the second coordinate space.

8. The computer readable storage medium of claim 7, wherein the computer program causes the system further to:
  calculate a transform from the interventional medical device identified in the second coordinate space to the segmented representation of the interventional medical device in the second coordinate space, and
  register the second coordinate space to the first coordinate space based on the transform.

9. A method for tracking location of an interventional medical device in an interventional medical procedure, the method comprising:
  identifying, using optical shape sensing signals received via an interface, a shape of an optical shape sensing device which has a shape that conforms to a shape of the interventional medical device during the interventional medical procedure;
  identifying the interventional medical device in a first coordinate space of a first imaging system that images the interventional medical device in a first imaging mode during the interventional medical procedure, based on identifying the shape of the optical shape sensing device;
  registering the interventional medical device to the first coordinate space;
  identifying the interventional medical device in a second coordinate space of a second imaging system that images the interventional medical device in a second imaging mode during the interventional medical procedure;
  registering the first coordinate space of the first imaging system to the second coordinate space of the second imaging system;
  segmenting the interventional medical device in the second coordinate space to obtain a segmented representation of the interventional medical device in the second coordinate space;
  registering the interventional medical device to the second coordinate space using the segmented representation of the interventional medical device; and
  re-registering the interventional medical device to the first coordinate space based on registering the interventional medical device to the second coordinate space.

10. The method of claim 9, further comprising:
rendering the segmented representation of the interventional medical device in the second coordinate space, and
repeating the segmenting, the registering of the interventional medical device to the second coordinate space and the re-registering of the interventional medical device to the first coordinate space.

11. The method of claim 10,
wherein the segmenting, the registering of the interventional medical device to the second coordinate space and the re-registering of the interventional medical device to the first coordinate space are performed based on a user selection of the interventional medical device in the second coordinate space.

12. The method of claim 10,
wherein the repeating is automatically performed periodically.

13. The method of claim 10, further comprising:
detecting that a location of the interventional medical device in an image in the second coordinate space has moved from a location of the segmented representation of the interventional medical device, and
wherein the segmenting, the registering of the interventional medical device to the second coordinate space and the re-registering of the interventional medical device to the first coordinate space are performed automatically based on the detecting.

14. The method of claim 9, further comprising:
calculating a transform from the interventional medical device identified in the second coordinate space to the segmented representation of the interventional medical device in the second coordinate space, and
registering the second coordinate space to the first coordinate space based on the transform.

15. The method of claim 14, further comprising:
detect a selection of the interventional medical device in an image from the second imaging system, and search for the interventional medical device in a region of the image proximate to the selection, and
wherein the transform is calculated by translating a distal portion of the interventional medical device in the image to match a corresponding distal portion of the interventional medical device in the segmentation.

* * * * *